US011436304B1

(12) United States Patent
Birgenheier et al.

(10) Patent No.: US 11,436,304 B1
(45) Date of Patent: Sep. 6, 2022

(54) AUTOMATED HEALTHCARE TYPE-SPECIFIC PATIENT REFUNDS

(71) Applicant: Wells Fargo Bank, N.A., San Francisco, CA (US)

(72) Inventors: Jason Robert Birgenheier, Las Vegas, NV (US); Mary C. St. John, Jr., Charlotte, NC (US)

(73) Assignee: Wells Fargo Bank, N.A., San Francisco, CA (US)

( * ) Notice: Subject to any disclaimer, the term of this patent is extended or adjusted under 35 U.S.C. 154(b) by 390 days.

(21) Appl. No.: 15/715,736

(22) Filed: Sep. 26, 2017

(51) Int. Cl.
*G06Q 40/06* (2012.01)
*G06F 19/00* (2018.01)
*G06Q 50/22* (2018.01)
*G16H 10/60* (2018.01)

(52) U.S. Cl.
CPC .......... *G06F 19/328* (2013.01); *G06Q 50/22* (2013.01); *G16H 10/60* (2018.01)

(58) Field of Classification Search
CPC ....... G06F 19/328; G16H 10/60; G06Q 50/22
See application file for complete search history.

(56) References Cited

U.S. PATENT DOCUMENTS

| 10,719,581 B2 * | 7/2020 | Lacy ................. G06Q 30/04 |
| 2007/0282740 A1 * | 12/2007 | Wendt .............. G06Q 30/00 705/39 |
| 2011/0258004 A1 * | 10/2011 | Dean ............... G06Q 10/10 705/4 |
| 2012/0239560 A1 * | 9/2012 | Pourfallah .......... G06Q 50/22 705/40 |

FOREIGN PATENT DOCUMENTS

WO    WO-2015044457 A1 *   4/2015   .......... G06Q 40/123

OTHER PUBLICATIONS

BCBS Companion Guide to X12 5010 Transactions—837 Institutional Health Care Claims v3.4, 2010 (Year: 2010).*
HIPAA EDI Companion Guide 835 Electronic Remittance Advice, version 2.0, Nov. 18, 2013 (Year: 2013).*
Marvin Sirbu, Credits and debits on the Internet, Feb. 1997, IEEE, web, 23-29 (Year: 1997).*

* cited by examiner

*Primary Examiner* — I Jung Liu
(74) *Attorney, Agent, or Firm* — Schwegman Lundberg & Woessner, P.A.

(57) ABSTRACT

Systems and methods may generally provide a demographic-based type-specific patient refund, facilitated by a structured data element, to a responsible party for overpayment made for healthcare services. An example method may include receiving a formatted claim file including an amount paid, receiving an amount owed by a responsible party, determining a refund amount based on the amount paid and the amount owed, and generating a formatted remittance file including the structured data element identifying the refund amount. The method may include determining a refund type, for example, based on at least one demographic factor of the responsible party, or providing, using information from the structured data element, the refund amount to the responsible party, such as via the refund type.

20 Claims, 5 Drawing Sheets

AUTOMATED HEALTHCARE TYPE-SPECIFIC PATIENT REFUNDS

BACKGROUND

Paying for healthcare services is often painful not just for patients, but also for healthcare providers themselves when refunds must be issued. Typically, refunds are determined manually in a time consuming process that often takes place months after services are rendered. Healthcare providers have attempted to rely on historical claims and remittance data to determine in advance what a healthcare payer will owe, while using historical remittance data to determine what a patient responsibility amount is owed. However, these estimates are frequently incorrect and result in overcharges by the healthcare providers and refunds owed to patients. In order to provide refunds, some current techniques rely on healthcare providers retaining paper receipts to later compare balances or require other burdensome accounting practices.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
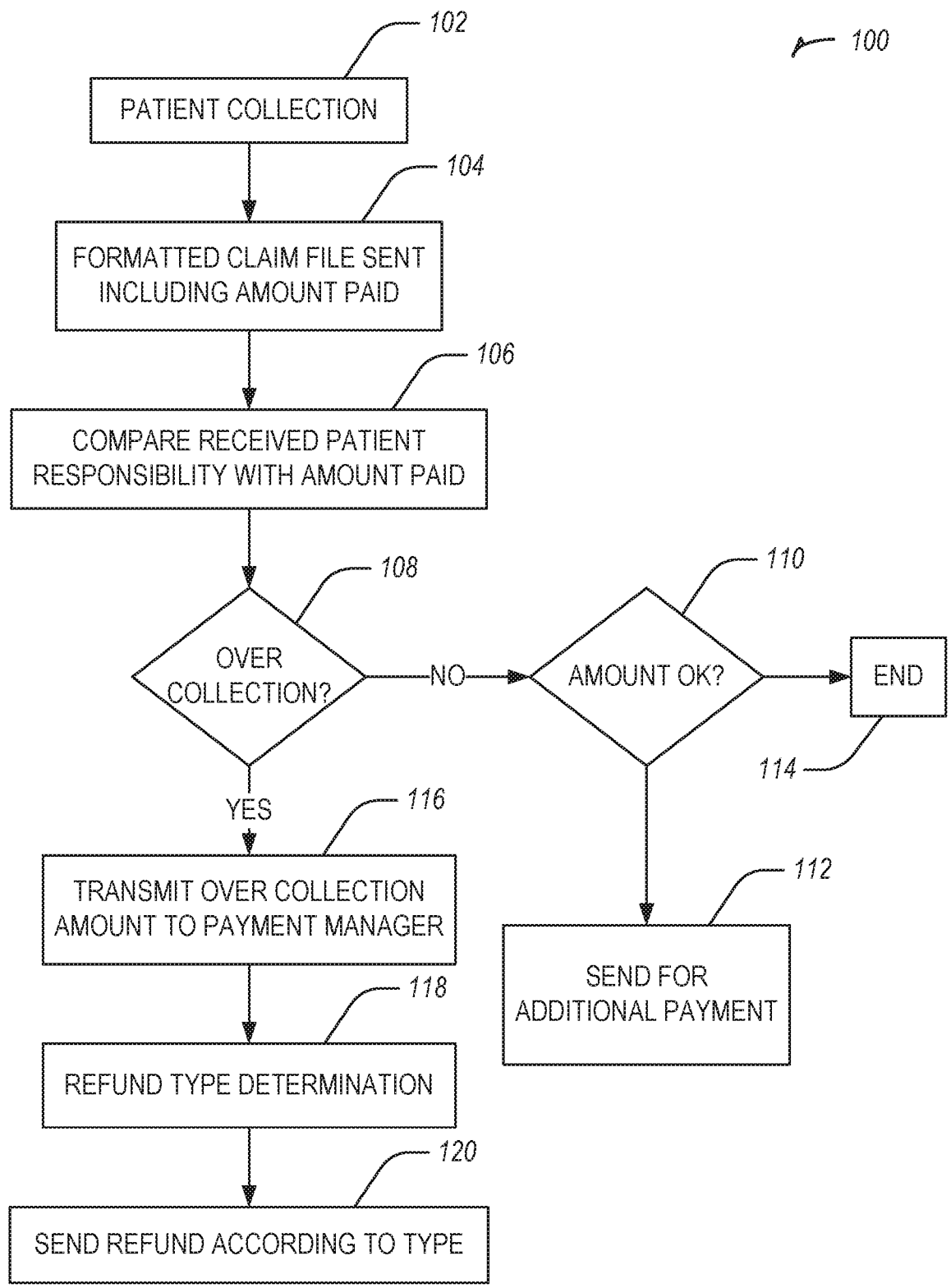
FIG. 1 illustrates a flowchart showing an automated patient refund process in accordance with some embodiments.

The healthcare industry is complex, involving healthcare providers, insurance companies (healthcare payers), and patients having many different backgrounds and preferences. Patients who have insurance typically are asked to provide insurance details at a time of service by a healthcare provider. The healthcare provider then determines, using payment guidelines, insurance details, services rendered, or other details, an amount likely to be owed by the patient after the healthcare provider pays an insured amount. After services are rendered by the healthcare provider, the healthcare provider sends information regarding the services, patient, etc., to the healthcare payer. The healthcare payer determines an amount covered by insurance, and a remaining amount owed by the patient. Typically, the healthcare provider will take a payment from the patient at the time of service, the payment including an estimated amount to be due. Eventually, the amount determined (by the healthcare payer) owed by the patient is sent to the healthcare provider. The healthcare provider may determine an amount to be refunded to the patient based on the amount paid at the time of service and the amount determined to be owed. The patient is then refunded that amount.

The systems and methods described herein provide an automated refund to a responsible party (e.g., the patient, the patient's guardian, etc.). These systems and methods may avoid further healthcare provider input after the service is performed and the initial payment is collected. In an example, the automated refund may be provided using a specific type of payment processing, such as based on patient preference or demographics. The collected patient balance may be sent to the healthcare payer or an evaluator of the claim, such as in the original claim from the healthcare provider, such that the collected patient balance may be used to determine whether the patient has over or under paid. The evaluator may automatically determine, after receiving a response from the healthcare payer, an amount to be refunded, and issue the refund using the specific type of payment processing to be used for the particular patient. For example, the refund may be issued to an original payment method (e.g., credit card, debit card, gift card, etc.). When the refund is not issuable to the original payment type (e.g., cash paid, credit card information not stored, credit card closed, etc.), the refund may be issued according to a specific type based on patient preference or demographic information.

According to some metrics, typical refunds to patients are around $45 dollars, with some coming in as much as $5,000, and many being around $10. There is great inconvenience to patients due to the time delay, which is typically around four weeks, to receive a refund. There is also inconvenience for the healthcare provider given the need to retain receipts and careful accounting, as well as overhead to issue the refunds. Patients in the healthcare industry have entirely diverse demographics, and each individual may prefer a particular type of payment when a refund is to be issued. For example, various factors may contribute to the types of refunds that may be possible or preferred, including a quickest payment method, a patient-demographic based method, limits on collecting patient information, technical restrictions, reconcilement, fees, or the like. Further details on types of refunds, restrictions, and demographics are described below.

FIG. 1 illustrates a flowchart showing an automated patient refund process 100 in accordance with some embodiments. The process 100 includes a healthcare provider (e.g., a doctor's office) collecting payment at patient collection block 102, such as at a point of sale (POS) device, such as a credit card reader, or collecting cash or a check. The process 100 includes creating and sending a claim file, such as an 837 claim file that includes the amount paid in a specified segment or data element of the 837 claim file. The claim file is received by a processing entity, which compares the claim file to an amount owed. The amount owed may be received by the processing entity from a healthcare payer (e.g., an insurance company) at block 106.

The process 100 includes determining at decision block 108 whether an overpayment has been made. When an overpayment has not been made, the process 100 continues at decision block 110. Decision block 110 include determining whether the amount paid is correct, and if so, ending the process 100 at block 114. If the amount paid is insufficient, an indication is sent to the healthcare provider to obtain additional payment at block 112.

When an overpayment has been made, the process 100 continues at block 116. Block 116 includes transmitting an over collection amount to a payment manager, such as an entity to issue a refund. The payment manager may determine, at block 118, a refund type. The refund type may be determined based on demographics (e.g., age, location, credit score, education level, career, financial sophistication, number of accounts, type of accounts, a predetermined preferred payment type, or the like). After the refund type is determined, the process 100 proceeds to block 120 where a refund is issued according to the type. In an example, a refund type may include a check sent by mail, an e-check, a wire or balance transfer, a prepaid gift card or balance mailed or emailed, a refund to an original payment type (e.g., a credit card, a debit card, a prepaid card, a gift card, etc.), a transfer to an app, a direct deposit to an account, a credit for future services, or the like.

The process 100 provides an automated technique to allow for more precise and timely refunds to be provided to patients in a refund type that is more convenient and personalized than a typical refund. Another advantage of the process 100 is in providing improved electronic remittance advice (ERA) processing by identifying relevant data at each point in the process 100. Additionally, patient satisfaction and confidence in the healthcare provider is improved using the process 100.

Referring now in more detail to blocks 104 and 106, additional details are provided below related to formatted claim files. In an example, a formatted claim file may include claim and remittance data elements, either of which may include subscriber and patient demographic data, such as name, address, date of birth or age, a patient account number, or the like. Additional structured data elements may be referred to as segments, such as a claim adjustment segment (CAS) in a 837 or 835 format file (described in more detail below with respect to Tables 1-4). The CAS segment may be populated to include patient collected balance using a patient responsibility (PR) code. The remittance data may reference the CLP segment (in the 835 format file) and the CAS segments (in the 837 or the 835 format files) to acknowledge the patient responsibility as reported by the payer, and may include coordination of additional benefits. The 837 and 835 file formats may be formatted according to a governing body, such as an X12 committee of the American National Standards Institute (ANSI).

TABLE 1

837 Format Description - Subscriber Information
837 Loop 2010BA - Subsciiber information

| Segment | Data Element | Name | Usage |
|---|---|---|---|
| NM1 | NM103 | Subscriber Last Name | Required |
|  | NM104 | Subscriber First Name | Required |
|  | NM105 | Subciber Middle Name | Required |
| N3 | N301 | Subciber Address Line | Required |
|  | N302 | Subciber Address Line | Required |
| N4 | N401 | Subciber City name | Required |
|  | N402 | Subciber State Code | Required |
|  | N403 | Subciber Zip Code | Required |
|  | N404 | Subciber Country Code | Required |
| DMG | DMG02 | Subciber Birth Date | Required |

TABLE 2

837 Format Description - Patient Information
837 Loop 2010CA - Patient Information

| Segment | Data Element | Name | Usage |
|---|---|---|---|
| NM1 | NM103 | Patient Last Name | Required |
|  | NM104 | Patient First Name | Required |
|  | NM105 | Patient Middle Name | Required |
| N3 | N301 | Patient Address Line | Required |
|  | N302 | Patient Address Line | Required |
| N4 | N401 | Patient City name | Required |
|  | N402 | Patient State Code | Required |
|  | N403 | Patient Zip Code | Required |
|  | N404 | Patient Country Code | Required |
| DMG | DMG02 | Patient Birth Date | Required |

TABLE 3

837 Format Description - Other Payer Information
837 Loop 2320 - Other Payer Information

| Segment | Data Element | Name | Usage |
|---|---|---|---|
| CAS | CAS01 | Claim Adjustment Group Code | Required |
|  | CAS02 | Claim Adjustment Reason | Required |
|  | CAS03 | Monetary Amount | Required |

After an episode of care, which may include a payment by the patient to cover their co-payment or deductible, the 837 file is compiled and then electronically sent to the healthcare payer. The 837 claim file is the electronic format for sending the bill of services including information about the service or other patient information to the payer. A computing system or service of the healthcare payer processes the claim, and then adjudicates how much of the amount due is the responsibility of the healthcare payer and how much is the responsibility of the patient, and may include how much of the bill is an overcharge or incorrect charge (e.g., is rejected or is the responsibility of the healthcare provider). This information is then sent in a remittance file to an evaluator to determine whether there was an over collection (108). In an example, the CAS01 data element in Loop 2320 of the 837 file may indicate patient responsibility (PR) to identify that the amount in CAS03 is the responsibility of the patient or the responsible party.

In an example, the patient information and the subscriber information (e.g., the responsible party or the person providing the insurance) may be different. For example, the patient may be a dependent and have a guardian responsible for making payments, the patient may be on a spouse's insurance, the patient may have borrowed a credit card from a friend or used a parent's check to make the payment (in these two cases, the refund may still go back to the patient, since the patient may have arranged to pay the friend or parent back in a different way), or the like. The responsible party is the party that is due the refund. In an example, the refund type determination 118 may occur after the responsible party is determined.

There is a segment in the 837 file that describes how much money was collected from the patient, the CAS03—Monetary Amount. The patient collected balance segment descriptor CAS01 indicates a claim adjustment group code, and CAS02 indicates a reason. These codes are used to indicate that the patient responsibility is the amount in CAS03, which is equal to the amount the responsible party paid at the time of service.

In order to issue a refund, the demographics of the patient may be used to determine whether the patient is the responsible party. In an example, information provided in Table 1 may be compared to the information provided in Table 2 to determine whether the patient is the responsible party. In another example, information from Table 2 may be used to determine, for example, whether the patient is a minor child. Further demographic information may be extracted from Tables 1 or 2 to determine a refund type to be used. For example, when the patient is a minor child, a refund may be sent to the child's guardian. In another example, when the patient is over a predetermined age, (e.g., older than 70), a check may be issued instead of a pre-paid debit card. Other situational rules may be implemented to determine the refund type and dynamically deliver the refund via the determined refund type.

After the 837 format file is sent to the healthcare payer, the healthcare payer sends back information that may be compiled in a 835 format file (as described in Table 4, below). The data from the healthcare provider may include a patient responsibility flag and an amount owed by the patient (e.g., the CAS03 data element, in the 835 format file, which may be formatted similarly or the same as the CAS03 data element of the 837 format file previously sent to the healthcare payer, which included the amount actually paid by the patient). With this flow through, an evaluator receiving both the 837 format file with a patient amount paid to the healthcare provider and the 835 format file with an amount determined (by the healthcare provider) to be owed by the patient, may determine an overpayment (e.g., when the CAS03 amount in the 835 format file exceeds the CAS03 amount in the 837 format file). The overpayment may be used as a basis for a refund, which may be issued according to a determined refund type. The patient responsibility flag may be used to verify that the amounts in the CAS03 data elements of the 837 and 835 format files are the patient amounts, since other amounts owed by other parties (e.g., healthcare payer responsibility or healthcare provider 'responsibility' or denied coverage, etc.) may be sent in the 837 or 835 format files.

TABLE 4

835 Format Description
835 Loop 2100

| Segment | Data Element | Name | Usage |
|---------|--------------|------|-------|
| CLP | CLP05 | Patient Responsibility | Required |
| CAS | CAS01 | Claim Adjustment Group Code | Required |
|  | CAS02 | Claim Adjustment Reason | Required |
|  | CAS03 | Monetary Amount | Required |

In an example, after the refund is sent according to the type 120, the 835 format file may be adjusted to identify that the refund has been issued. For example, the CAS03 amount in the 835 format file may be adjusted to be equal to the CAS03 amount in the 837 format file, for example before sending the 835 format file to the healthcare provider. In another example, a flag indicating a refund has already been paid may be added. In yet another example, a notification (e.g., by email, mail, etc.) may be sent with the 835 format file to indicate the refund has occurred.

Below in Tables 5-11, additional data elements from an 837 standard are described with other codes and formats that may be used to implement the systems and methods described herein. Some segments may be repeated from Tables 1-3 above or may include additional information.

TABLE 5

837 Format Description - Full Subscriber Information

| Element Identifier | Description | ID | Min. Max. | Usage | Reg. Loop | Loop Repeat | Values |
|---|---|---|---|---|---|---|---|
| NM1 | SUBSCRIBER NAME |  | 1 | R | 2010BA | 1 |  |
| NM101 | Entity Identifier Code | ID | 2-3 | R |  |  | IL |
| NM102 | Entity Type Qualifier | ID | 1-1 | R |  |  | 1, 2 |
| NM103 | Subscriber Last Name | AN | 1-60 | R |  |  |  |
| NM104 | Subscriber First Name | AN | 1-35 | S |  |  |  |
| NM105 | Subscriber Middle Name | AN | 1-25 | S |  |  |  |
| NM106 | Name Prefix | AN | 1-10 | N/U |  |  |  |
| NM107 | Subscriber Name Suffix | AN | 1-10 | S |  |  |  |
| NM108 | Identification Code Qualifier | ID | 1-2 | R |  |  | II, MI |
| NM109 | Subscriber Primary Identifier | AN | 2-80 | R |  |  |  |
| NM110 | Entity Relationship Code | ID | 2-2 | NU |  |  |  |
| NM111 | Entity Identifier Code | ID | 2-3 | NU |  |  |  |
| NM112 | Name Last or Organization Name | AN | 1-60 | NU |  |  |  |
| N3 | SUBSCRIBER ADDRESS |  | 1 | S | 2010BA |  |  |
| N301 | Subscriber Address Line | AN | 1-55 | R |  |  |  |
| N302 | Subscriber Address Line | AN | 1-55 | S |  |  |  |

TABLE 5-continued

837 Format Description - Full Subscriber Information

| Element Identifier | Description | ID | Min. Max. | Usage | Reg. Loop | Loop Repeat | Values |
|---|---|---|---|---|---|---|---|
| N4 | SUBSCRIBER CITY/STATE/ZIP CODE | | 1 | S | 2010BA | | |
| N401 | Subscriber City Name | AN | 2-30 | R | | | |
| N402 | Subscriber State Code | ID | 2--2 | S | | | |
| N403 | Subscriber Postal Zone or ZIP Code | ID | 3-15 | S | | | |
| N404 | Subscriber Country Code | ID | 2-3 | 5 | | | |
| N405 | Location Qualifier | ID | 1-2 | NU | | | |
| N406 | Location Identifier | AN | 1-30 | NU | | | |
| N407 | Country Subdivision Code | ID | 1-3 | S | | | |
| DMG | SUBSCRIBER DEMOGRAPHIC INFORMATION | | 1 | S | 2010BA | | |
| DMG01 | Date Time Period Format Qualifier | ID | 2-3 | R | | | D8 |
| DMG02 | Subscriber Birth Date | AN | 1-35 | R | | | CCYYMMDD |
| DMG03 | Subscriber Gender Code | ID | 1-1 | R | | | F, M, U |
| DMG04 | Marital Status Code | ID | 1-1 | NU | | | |
| DMG05 | Race or Ethnicity Code | ID | 1-1 | NU | | | |
| DMG06 | Citizen ship Status Code | ID | 1-2 | NU | | | |
| DMG07 | Country Code | ID | 2-3 | NU | | | |
| DMG08 | Basis of Verfication Code | ID | 1-2 | NU | | | |
| DMG09 | Quantity | R | 1-15 | NU | | | |
| DMG10 | Code List Qualifier Code | ID | 1-3 | NU | | | |
| DMG11 | Industry Code | AN | 1-30 | NU | | | |

TABLE 6

837 Format Description - Payer information (e.g., self-insured)

| Element Identifier | Description | ID | Min. Max. | Usage | Reg. Loop | Loop Repeat | Values |
|---|---|---|---|---|---|---|---|
| NM1 | PAYER NAME | | 1 | IR | 2010BB | 1 | |
| NM101 | Entity Identifier Code | ID | 2-3 | R | | | PR |
| NM102 | Entity Type Qualifier | ID | 1-1 | R | | | 2 |
| NM103 | Payer Name | AN | 1-60 | R | | | |
| NM104 | Name First | AN | 1-35 | NU | | | |
| NM105 | Name Middle | AN | 1-25 | NU | | | |
| NM106 | Name Prefix | AN | 1-10 | NU | | | |
| NM107 | Name Suffix | AN | 1-10 | NU | | | |
| NM108 | Identification Code Qualifier | ID | 1-2 | R | | | PI, XV |
| NM109 | Payer Identifier | AN | 2-80 | R | | | |
| NM110 | Entity Relationship Code | ID | 2-2 | NU | | | |
| NM111 | Entity Identifier Code | ID | 2-3 | NU | | | |
| NM112 | Name Last or Organization Name | AN | 1-60 | NU | | | |

TABLE 6-continued

| 837 Format Description - Payer information (e.g., self-insured) | | | | | | | | | |
|---|---|---|---|---|---|---|---|---|---|
| Element Identifier | Description | ID | Min. | Max. | Usage | Reg. Loop | Loop Repeat | Values | |
| N3 | PAYER ADDRESS | | | 1 | S | 2010BB | | | |
| N301 | Payer Address Line | AN | 1-55 | | R | | | | |
| N302 | Payer Address Line | AN | 1-55 | | S | | | | |
| N4 | PAYER CITY/STATE/ZIP CODE | | | 1 | R | 2010BB | | | |
| N401 | Payer City Name | AN | 2-30 | | R | | | | |
| N402 | Payer State Code | ID | 2-2 | | S | | | | |
| N403 | Payer Postal Zone or ZIP Code | ID | 3-15 | | S | | | | |
| N404 | Payer Country Code | ID | 2-3 | | S | | | | |
| N405 | Location Qualifier | ID | 1-2 | | NU | | | | |
| N406 | Location Identifier | AN | 1-30 | | NU | | | | |
| N407 | Country Subdivision Code | ID | 1-3 | | S | | | | |

TABLE 7

| 837 Format Description - Full Patient information | | | | | | | | | |
|---|---|---|---|---|---|---|---|---|---|
| Element Identifier | Description | ID | Min. | Max. | Usage | Reg. Loop | Loop Repeat | Values | |
| NM1 | PATIENT NAME | | | 1 | A | 2010CA | 1 | | |
| NM101 | Entity Identifier Code | ID | 2-3 | | A | | | OC | |
| NM102 | Entity Type Qualifier | ID | 1-1 | | A | | | 1 | |
| NM103 | Patient Last Name | AN | 1-60 | | A | | | | |
| NM104 | Patient First Name | AN | 1-35 | | S | | | | |
| NM105 | Patient Middle Name | AN | 1-25 | | S | | | | |
| NM106 | Name Prefix | AN | 1-10 | | NU | | | | |
| NM107 | Patent Name Suffix | AN | 1-10 | | S | | | | |
| NM108 | Identification Code Qualifier | ID | 1-2 | | NU | | | | |
| NM109 | Patient Primary Identifier | AN | 2-80 | | NU | | | | |
| NM110 | Entity Relationship Code | ID | 2-2 | | NU | | | | |
| NM111 | Entity Identifier Code | ID | 2-3 | | NU | | | | |
| NM112 | Name Last or Organization Code | AN | 1-60 | | NU | | | | |
| N3 | PATIENT ADDRESS | | | 1 | R | 2010CA | | | |
| N301 | Patient Address Line | AN | 1-55 | | R | | | | |
| NM302 | Patient Address Line | An | 1-55 | | S | | | | |
| N4 | PATIENT CITY/STATE/ZIP CODE | | | 1 | R | 2010CA | | | |
| N401 | Patient City Name | AN | 2-30 | | R | | | | |
| N402 | Patient State Code | ID | 2-2 | | S | | | | |
| N403 | Patient Postal Zone or Zip Code | ID | 3-15 | | S | | | | |
| N404 | Patient Country Code | ID | 2-3 | | S | | | | |

TABLE 7-continued

837 Format Description - Full Patient information

| Element Identifier | Description | ID | Min. Max. | Usage | Reg. Loop | Loop Repeat | Values |
|---|---|---|---|---|---|---|---|
| N405 | Location Qualifier | ID | 1-2 | NU | | | |
| N406 | Location Identifier | AN | 1-30 | NU | | | |
| N407 | Country Subdivision Code | ID | 1-3 | S | | | |
| DMG | PATIENT DEMOGRAPHIC INFORMATION | | 1 | R | 2010CA | | |
| DMG01 | Date Time Period Format Qualifier | ID | 2-3 | R | | | D8 |
| DMG02 | Patent Birth Date | AN | 1-35 | R | | | CCYYMMDD |
| DMG03 | Patent Gender Code | ID | 1-1 | R | | | F, M, U |
| DMG04 | Marital Status Code | ID | 1-1 | NU | | | |
| DMG05 | Race or Ethnicity Code | ID | 1-1 | NU | | | |
| DMG06 | Citizenship Status Code | ID | 1-2 | NU | | | |
| DMG07 | Country Code | ID | 2-3 | NU | | | |
| DMG08 | Basis of Verification Code | ID | 1-2 | NU | | | |
| DMG09 | Quantity | R | 1-15 | NU | | | |
| DMG10 | Code List Qualifier Code | ID | 1-3 | NU | | | |
| DMG11 | Industry Code | AN | 1-30 | NU | | | |

TABLE 8

837 Format Description - Claim Information (ie.g., for a service at the healthcare provider)

| | | | | | | | |
|---|---|---|---|---|---|---|---|
| CLM | CLAIM INFORMATION | | | 1 | R | 2300 | 100 |
| CLM01 | Patient Account Number | | AN | 1-38 | R | | |
| CLM02 | Total Claim Charge Amount | | R | 1-18 | R | | |
| CLM03 | Claim Filing Indicator Code | | ID | 1-2 | NU | | |
| CLM04 | Non-Institutional Claim Type Code | | ID | 1-2 | NU | | |
| CLM05 | HEALTH CARE SERVICE LOCATION INFORMATION | | | | R | | |
| CLM05-1 | Facility Type Code | | AN | 1-2 | R | | |
| CLM05-2 | Facility Code Qaulifier | | ID | 1-2 | R | | A |
| CLM05-3 | Claim Frequency Code | | ID | 1-1 | R | | |
| CLM06 | Provider or Supplier Signature Indicator | | ID | 1-1 | NU | | N.Y. |
| CLM07 | Medicare Assignment Code | | ID | 1-1 | R | | A, B, C |
| CLM08 | Benefits Assignment Certification Indicator | | ID | 1-1 | R | | N, W, Y |
| CLM09 | Release of Information Code | | ID | 1-1 | R | | I, Y |
| CLM10 | Patient Signature Source Code | | ID | 1-1 | S | | P |
| CLM11 | RELATED CAUSES INFORMATION | | | | NU | | |
| CLM12 | Special Program Indicator | | ID | 2-3 | S | | 02, 03, 05, 09 |
| CLM13 | Yes/No Condition or Response Code | | ID | 1-1 | NU | | |

TABLE 8-continued

837 Format Description - Claim Information (ie.g., for a service at the healthcare provider)

| CLM | CLAIM INFORMATION | | 1 | R | 2300 | 100 |
|---|---|---|---|---|---|---|
| CLM14 | Level of Service Code | ID | 1-3 | NU | | |
| CLM15 | Yes/No Condition or Response Code | ID | 1-1 | NU | | |
| CLM16 | Participation Agreement | ID | 1-1 | NU | | |
| CLM17 | Claim Status Code | ID | 1-2 | NU | | |
| CLM18 | Yes/No Condition or Response Code | ID | 1-1 | NU | | |
| CLM19 | Claim Submission Reason Code | ID | 2-2 | NU | | |
| CLM20 | Delay Reason Code | ID | 1-2 | S | | 1, 2, 3, 4, 5, 6, 7, 8, 9, 10, 11, 15 |

TABLE 9

837 Format Description Estimated Payment Information

| AMT | PATIENT ESTIMATED AMOUNT DUE | | 1 | S | 2300 | |
|---|---|---|---|---|---|---|
| AMT01 | Amount Qualifier Code | ID | 1-3 | R | | F3 |
| AMT02 | Patient Responsibility Amount | R | 1-18 | R | | |
| AMT03 | Credit/Debit Flag Code | ID | 1-1 | NU | | |

TABLE 10

837 Format Description - Amount Paid By Responsible Party and Other Subscriber Information

| CAS | CLAIM LEVEL ADJUSTMENTS | | 5 | S | 2320 | |
|---|---|---|---|---|---|---|
| CAS01 | Claim Adjustment Group Code | ID | 1-2 | R | | CO, CR, OA, PI, PR |
| CAS02 | Adjustment Reason Code | ID | 1-5 | R | | |
| CAS03 | Adjustment Amount | R | 1-18 | R | | |
| CAS04 | Adjustment Quantity | R | 1-15 | S | | |
| CAS05 | Adjustment Reason Code | ID | 1-5 | S | | |
| CAS06 | Adjustment Amount | R | 1-18 | S | | |
| CAS07 | Adjustment Quantity | R | 1-15 | S | | |
| CAS08 | Adjustment Reason Code | ID | 1-5 | S | | |
| CAS09 | Adjustment Amount | R | 1-18 | S | | |
| CAS10 | Adjustment Quantity | R | 1-15 | S | | |
| CAS11 | Adjustment Reason Code | ID | 1-5 | S | | |
| CAS12 | Adjustment Amount | R | 1-18 | S | | |
| CAS13 | Adjustment Quantity | R | 1-15 | S | | |
| CAS14 | Adjustment Reason Code | ID | 1-5 | S | | |
| CAS15 | Adjustment Amount | R | 1-18 | S | | |
| CAS16 | Adjustment Quantity | R | 1-15 | S | | |

TABLE 10-continued

837 Format Description - Amount Paid By Responsible Party and Other Subscriber Information

| | | | | | | |
|---|---|---|---|---|---|---|
| CAS17 | Adjustment Reason Code | ID | 1-5 | S | | |
| CAS18 | Adjustment Amount | R | 1-18 | S | | |
| CAS19 | Adjustment Quantity | R | 1-15 | S | | |
| AMT | COB PAYER PAID AMOUNT | | 1 | S | 2320 | |
| AMT01 | Amount Qualifier Code | ID | 1-3 | R | | D |
| AMT02 | Payer Paid Amount | R | 1-18 | R | | |
| AMT03 | Credit/Debit Flag Code | ID | 1-1 | NU | | |
| AMT | REMAINING PATIENT LIABILITY | | 1 | S | 2320 | |
| AMT01 | Amount Qualifier Code | ID | 1-3 | | | EAF |
| AMT02 | Remaining Patient Liability Amount | R | 1-18 | | | |
| AMT03 | Credit/Debit Flag Code | ID | 1-1 | | | |
| AMT | COB TOTAL NON-COVERED AMOUNT | | 1 | S | 2320 | |
| AMT01 | Amount Qualifier Code | ID | 1-3 | R | | A8 |
| AMT02 | Non-Covered Amount | R | 1-18 | R | | |
| AMT03 | Credit/Debit Flag Code | ID | 1-1 | NU | | |

TABLE 11

837 Format Description - Other Subscriber Information

| | | | | | | |
|---|---|---|---|---|---|---|
| NM1 | OTHER SUBSCRIBER NAME | | 1 | R | 2320A | 1 |
| NM101 | Entity Identifier Code | ID | 2-3 | R | | IL |
| NM102 | Entity Type Qualifier | ID | 1-1 | R | | 1, 2 |
| NM103 | Other Insured Last Name | AN | 1-60 | R | | |
| NM104 | Other Insured First Name | AN | 1-35 | S | | |
| NM105 | Other Insured Middle Name | AN | 1-25 | S | | |
| NM106 | Name Prefix | AN | 1-10 | NU | | |
| NM107 | Other Insured Name Suffix | AN | 1-10 | S | | |
| NM108 | Identification Code Qualifier | ID | 1-2 | R | | II, MI |
| NM109 | Other Insured Identifier | AN | 2-80 | R | | |
| NM110 | Entity Relationship Code | ID | 2-2 | NU | | |
| NM111 | Entity Identifier Code | ID | 2-3 | NU | | |
| NM112 | Name Last or Organization Name | AN | 1-60 | NU | | |
| N3 | OTHER SUBSCRIBER ADDRESS | | 1 | S | 2330A | |
| N301 | Other insured Address Line | AN | 1-55 | R | | |
| N302 | Other Insured Address Line | AN | 1-55 | S | | |
| N4 | OTHER SUBSCRIBER CITY/STATE/ZIP CODE | | 1 | R | 2330A | |
| N401 | Other insured City Name | AN | 2-30 | R | | |
| N402 | Other Insured State Code | ID | 2-2 | S | | |
| N403 | Other Insured Postal Zone or ZIP Code | ID | 3-15 | S | | |
| N404 | Subscriber Country Code | ID | 2-3 | S | | |
| N405 | Location Qualifier | ID | 1-2 | NU | | |
| N406 | Location Qualifier | AN | 1-30 | NU | | |
| N407 | Country Subdivision Code | ID | 1-3 | S | | |

TABLE 11-continued

837 Format Description - Other Subscriber Information

| | | | | | | |
|---|---|---|---|---|---|---|
| NM1 | OTHER PAYER NAME | | 1 | R | 2330B | 1 |
| NM101 | Entity Identifier Code | ID | 2-3 | R | | PR |
| NM102 | Entity Type Qualifier | ID | 1-1 | R | | 2 |
| NM103 | Other Payer Last or Organization Name | AN | 1-60 | R | | |
| NM104 | Name First | AN | 1-35 | NU | | |
| NM105 | Name Middle | AN | 1-25 | NU | | |
| NM106 | Name Prefix | AN | 1-10 | NU | | |
| NM107 | Name Suffix | AN | 1-10 | NU | | |
| NM108 | Identification Code Qualifier | ID | 1-2 | R | | PI, XV |
| NM109 | Other Payer Primary Identifier | AN | 2-80 | R | | |
| NM110 | Entity Relationship Code | NU | 2-2 | NU | | |
| NM111 | Entity Identifier Code | NU | 2-3 | NU | | |
| NM112 | Name Last or Organization Name | NU | 1-60 | NU | | |
| N3 | OTHER PAYER ADDRESS | | 1 | S | 2330B | |
| N301 | Other Payer Address line | AN | 1-55 | R | | |
| N302 | Other Payer Address line | AN | 1-55 | S | | |
| N4 | OTHER PAYER CITY/STATE/ZIP CODE | | 1 | R | 2330B | |
| N401 | Other Payer City Name | AN | 2-30 | R | | |
| N402 | Other Payer State Code | ID | 2-2 | S | | |
| N403 | Other Payer Postal Zone or ZIP Code | ID | 3-15 | S | | |
| N404 | Other Payer Country Code | ID | 2-3 | S | | |
| N405 | Location Qualifier | ID | 1-2 | NU | | |
| N406 | Location Identifier | AN | 1-30 | NU | | |
| N407 | Country Subdivision Code | ID | 1-3 | S | | |
| CAS | LINE ADJUSTMENT | | 5 | S | 2430 | |
| CAS01 | Claim Adjustment Group Code | ID | 1-2 | R | | CO, CR, OA, PI, PR |
| CAS02 | Adjustment Reason Code | ID | 1-5 | R | | |
| CAS03 | Adjustment Amount | R | 1-18 | R | | |
| CAS04 | Adjustment Quantity | R | 1-15 | S | | |
| CAS05 | Adjustment Reason Code | ID | 1-5 | S | | |
| CAS06 | Adjustment Amount | R | 1-18 | S | | |
| CAS07 | Adjustment Quantity | R | 1-15 | S | | |
| CAS08 | Adjustment Reason Code | ID | 1-5 | S | | |
| CAS09 | Adjustment Amount | R | 1-18 | S | | |
| CAS10 | Adjustment Quantity | R | 1-15 | S | | |
| CAS11 | Adjustment Reason Code | ID | 1-5 | S | | |
| CAS12 | Adjustment Amount | R | 1-18 | S | | |
| CAS13 | Adjustment Quantity | R | 1-15 | S | | |
| CAS14 | Adjustment Reason Code | ID | 1-5 | S | | |
| CAS15 | Adjustment Amount | R | 1-18 | S | | |
| CAS16 | Adjustment Quantity | R | 1-15 | S | | |
| CAS17 | Adjustment Reason Code | ID | 1-5 | S | | |
| CAS18 | Adjustment Amount | R | 1-18 | S | | |
| CAS19 | Adjustment Quantity | R | 1-15 | S | | |
| AMT | REMAINING PATIENT LIABILITY | | 1 | S | 2430 | |
| AMT01 | Amount Qualifier Code | ID | 1-3 | R | | EAF |
| AMT02 | Remaining Patient Liability Amount | R | 1-18 | R | | |
| AMT03 | Credit/Debit Flag Code | ID | 1-1 | NU | | |

In an example, the claim information provided in Table 8 may be used to extract demographic information to determine the refund type. For example, the claim information may include name, address, date of birth, social security number, patient account number, patient collected balance, etc., which may be used to determine the refund amount and the refund type.

Figure 2:
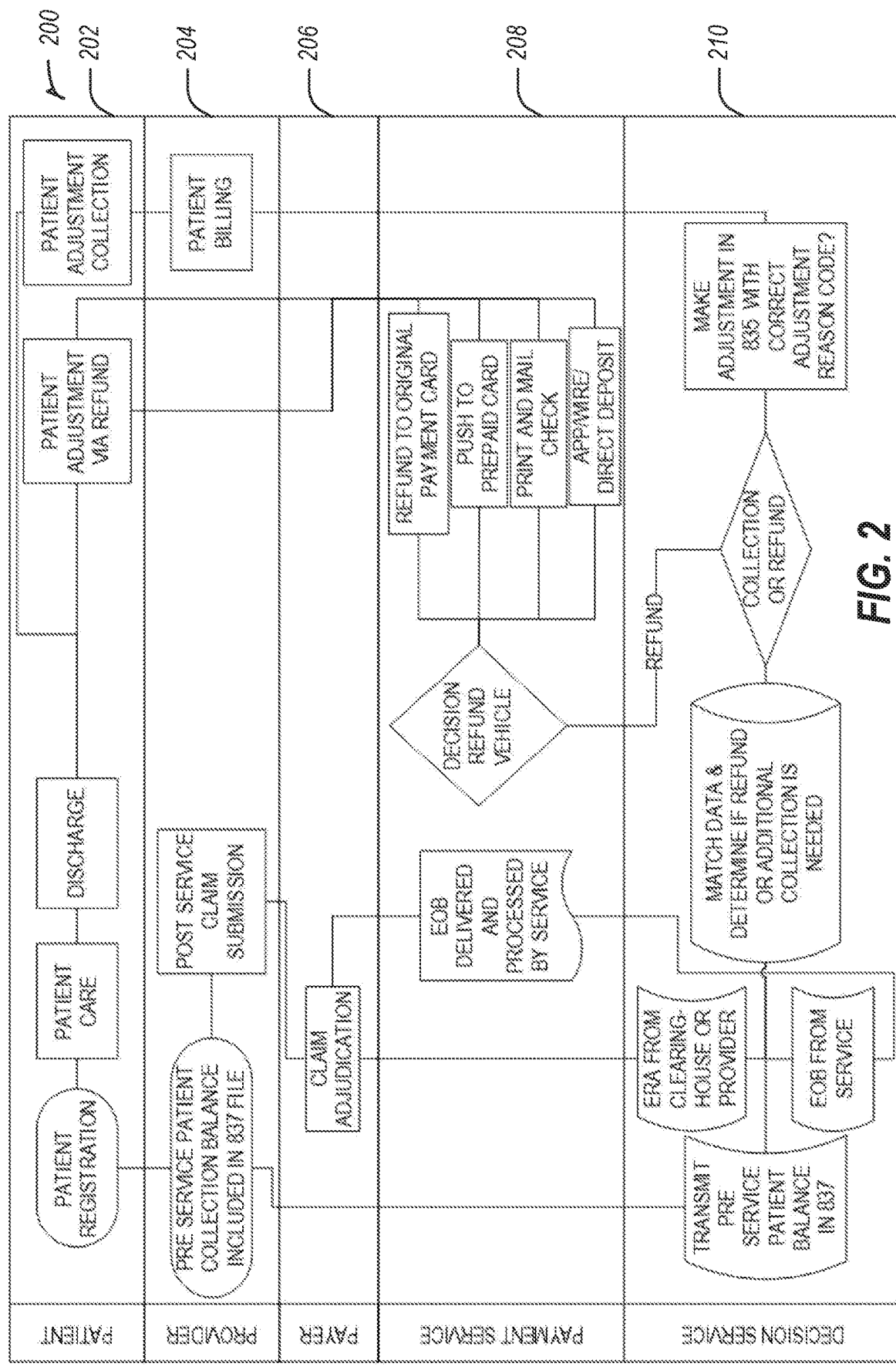
FIG. 2 illustrates a flowchart showing an automated delivery type determination process in accordance with some embodiments.

FIG. 2 illustrates a flowchart showing an automated delivery type determination process 200 in accordance with some embodiments. The process 200 includes a set of actions by a plurality of actors, including a patient 202, a provider 204, a payer 206, a payment service 208, and a decision service (i.e., evaluator) 210. Each actor depicted in the process 200 may perform actions as indicated, or actors may be merged (e.g., the payment service 208 and the decision service 210 may be one entity, or appear to be one entity to the payer 206, the provider 204, or the patient 202). In an example, some actors may never interact with other actors. For example, the patient 202 may never interact with the payer 206, or the provider may never interact with the payment service 208.

The process 200 may start with registration of the patient 202, patient care, or pre-service patient collection of balance to be included in an 837 file. In an example, aspects of the process 200 may occur concurrently or without directly flowing from other operations. For example, the patient may be discharged without regard to whether the claim has been adjudicated by the payer 206.

After the pre-service collection is performed by the provider 204, an 837 format file is created and sent to the decision service 210. There, a pre-service patient balance may be transmitted in an 837 format file (the same, modified, or different as the one sent by the provider 204), such as to a clearinghouse or provider. The clearinghouse, provider, or trading partner, may send the 837 format file to the payer 206 to perform a claim adjudication. The provider 204 may submit a post-service claim submission to the payer 206. The payer sends information including a claim adjudication to the payment service 208 for processing, which may forward the information to the decision service 210. The decision service 210 may receive the information as an 835 format file from the payment service 208 (which in turn may have received the 835 format file from the payer 206 or may have created it), or may create an 835 format file from the information. The decision service 210 may match data from the 837 file and the information from the payer 206 to determine whether a refund or additional collection is needed. When additional collection is needed, a notification may be sent to the patient 202, the provider 204, the payer 206, or the payment service 208 for further processing.

When a refund is to be issued, the decision service 210 alerts the payment service 208. The payment service 208 may determine a refund vehicle or type to determine how to issue the refund, and to whom (e.g., the patient or other responsible party). For example, the payment service 208 may determine whether to issue the refund to an original payment card (e.g., credit or debit), send the refund via a prepaid card, print and mail a check, send the refund via an app, wire transfer, direct deposit, or the like. After the type of refund is determined, the patient 202 may be directly sent the refund using the refund type (payment adjustment via refund). Optionally, the decision service 210 may make an adjustment in an 835 format file with an adjustment reason code or adjust an amount owed or paid by the patient to reflect the refund paid out to the patient 202. The adjusted 835 format file may be sent to the provider 204 for updating patient billing. In an example, when further collections are required, the patient 202 may be notified, for example from the provider 204 with a patient adjustment collection. In an example, the process 200 may be used to maximize ERA processing to obtain data needed to automatically determine an amount overpaid.

In an example, providers may be allowed to accept or reject calculated refunds. For example, an online service may be used to allow the provider to automatically receive information about a refund, such as an amount due. There may be extenuating circumstances that the provider has knowledge of outside of the 837/835 data flows that may influence the provider's ability or willingness to issue the refund. In an example, the provider may not modify the calculated amount, due to audit trail and adjustments that may be required, but may be allowed to reject or approve the refund for issuance. Once approved, the refund may be issued automatically, for example according to the refund type.

Figure 3:
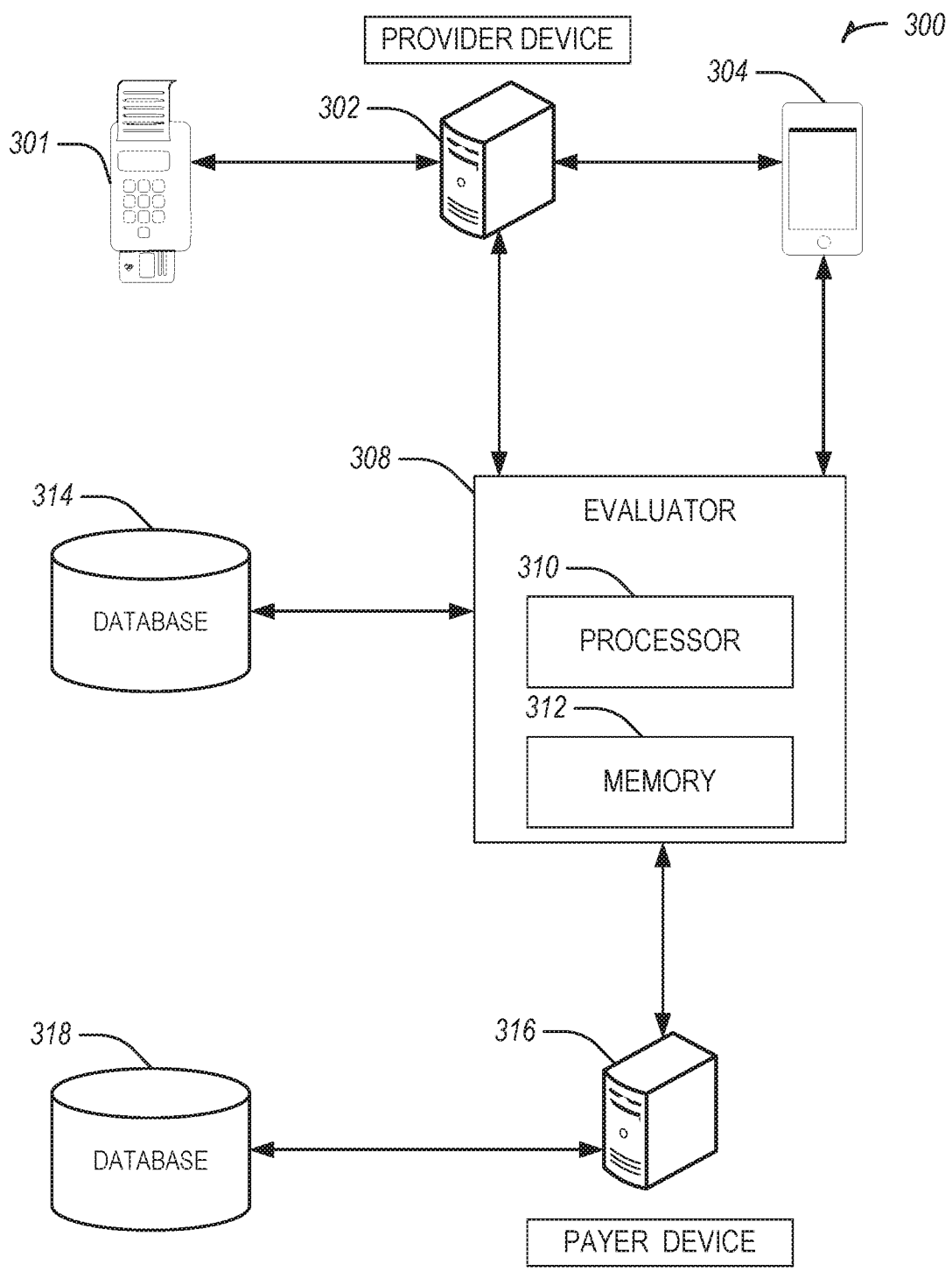
FIG. 3 illustrates a system for automated patient refund delivery according to a delivery type in accordance with some embodiments.

FIG. 3 illustrates a system 300 for automated patient refund delivery according to a delivery type in accordance with some embodiments. The system 300 includes a healthcare provider device 302, an evaluator 308 including a processor 310 and memory 312, and a healthcare payer device 316. The system 300 may include a payment processing device 301 in communication with the healthcare provider device 302 or a patient device 304, which may be in communication with the healthcare provider device 302 or the evaluator 308. The evaluator 308 or the payer device 316 may query databases 314 or 318, respectively. The system 300 may be used to provide a structured data element for processing patient refunds.

When querying the databases 314 or 318, the evaluator 308 or the payer device 316 respectively, may receive an 835 or 837 formatted file, or may receive information to populate an 835 or 837 formatted file. A portion of an example 835 format file is displayed below:
ISA*01*0000000000*01*0000000000*ZZ*ABCD
EFGHJKLMNO*ZZ*123456789012345*10
1127*1719*U*00400*000003438*0*P*>
GS*HP*EXAMPLECO*01017*20110315*1005*1*
X*004010X091A1
ST*835*07504123
BPR*H*5.75*C*NON************20110315
TRN*1*A04B001017.07504*1346000128
DTM*405*20110308
N1*PR*ADDRESS*XX*6457839886
N3*SUITE 101
N4*MINNEAPOLIS*MN*55403
REF*PQ*1017                                                          LX*1
CLP*444444*1*56.70*56.52*0*MC*00000006
55555555*53
NM1*QC*1*DOE*JOHN*S***MI*1333333
NM1*82*2*WECOVERWY
SVC5*****FI*346608640              REF*F8*A76B04054
SVC*HC:H0005:HF:H9*56.70*56.52**6
DTM*472*20110205                   CAS*CO*42*0.18*0
REF*6R*444444

A portion of an example 837 format file is displayed below:
ISA*01*0000000000*01*0000000000*ZZ*
ABCDEFGHIKLMNO*ZZ*123456789012345*10
1127*1719*U*00400*000003438*0*P*>
GS*HC*99999999999*888888888888*
20111219*1340*1377*X*005010X222
ST*837*0001*005010X222
BHT*0019*00*565743*20110523*154959*CH
NM1*41*2*EXAMPLECO*****46*496103
PER*IC*EDI
DEPT*EM*EMAIL@WEBSITE.COM*TE*3305551212
NM*40*2*PPO BLUE*****46*54771
HL*1**20*1
PRV*BI*PXC*333600000X
NM*85*2*EXAMPLE*****XX*123456789
N3*ADDRESS
N4*CHICAGO*IL*606930159
REF*EI*300123456
HL*2*1*22*1
SBR*P********BL
NM*IL*1*CUSTOMER*JOE****MN*YYX123456789

The databases 314 or 318 for example, may include a user name or address, which may be populated in the 835 or 837 file as seen above. When the 835 or 837 format files are populated, they may be interpreted by the evaluator 308 to automatically extract information. The extracted information may be used to determine whether a refund is due, what type of refund to issue when one is due, where to send the refund, who the responsible party is, whether to notify the payer device 316 or the provider device 302, etc.

In an example, the processor 310 may include one or more processors and may be coupled to the memory 312. The memory 312 may be a memory device containing instructions that, when executed by the one or more processors, cause the evaluator 308 to perform operations, such as those described below.

An operation may include receiving, from a service of the healthcare provider (e.g., the healthcare provider device 302), a formatted claim file including a segment indicating a payment responsibility and an amount paid. An operation may include receiving, from a service of a healthcare payer (e.g., the healthcare provider payer 316), information indicating an amount owed by a responsible party. An operation may include determining a refund amount based on the amount paid and the amount owed.

In an example, the operations include generating a formatted remittance file including the structured data element identifying the refund amount. In an example, the operations include determining a refund type based on at least one demographic factor of the responsible party. The demographics may include age, location, credit score, education level, career, financial sophistication, number of accounts, type of accounts, a predetermined preferred payment type, or the like. The refund amount may be provided, using information from the structured data element, to the responsible party via the refund type. For example, the refund type may include a check sent by mail, an e-check, a wire or balance transfer, a prepaid gift card or balance mailed or emailed, a refund to an original payment type (e.g., a credit card, a debit card, a prepaid card, a gift card, etc.), a transfer to an app, a direct deposit to an account, a credit for future services, or the like. For example, the refund type may be a check when the age of the responsible party exceeds a threshold, and a prepaid debit card when the age of the responsible party falls below the threshold or a second threshold (e.g., a check when the age is over 70, and a prepaid debit card when the age is under 40).

In an example, the formatted claim file is a standardized electronic data interchange (EDI) 837 formatted file and wherein the formatted remittance file is a standardized EDI 835 formatted file. In another example, the operations may include determining a responsible party to send the refund, wherein the responsible party is one of the patient or a guardian of the patient. The operations may include updating the formatted remittance file to adjust the amount owed by the patient to equal the amount paid minus the refund; and send the updated formatted remittance file to the healthcare provider. After the refund is paid, a confirmation may be sent by the evaluator 308 to the provider device 302 to confirm that the refund has been delivered, sent, or accepted by the patient.

Figure 4:
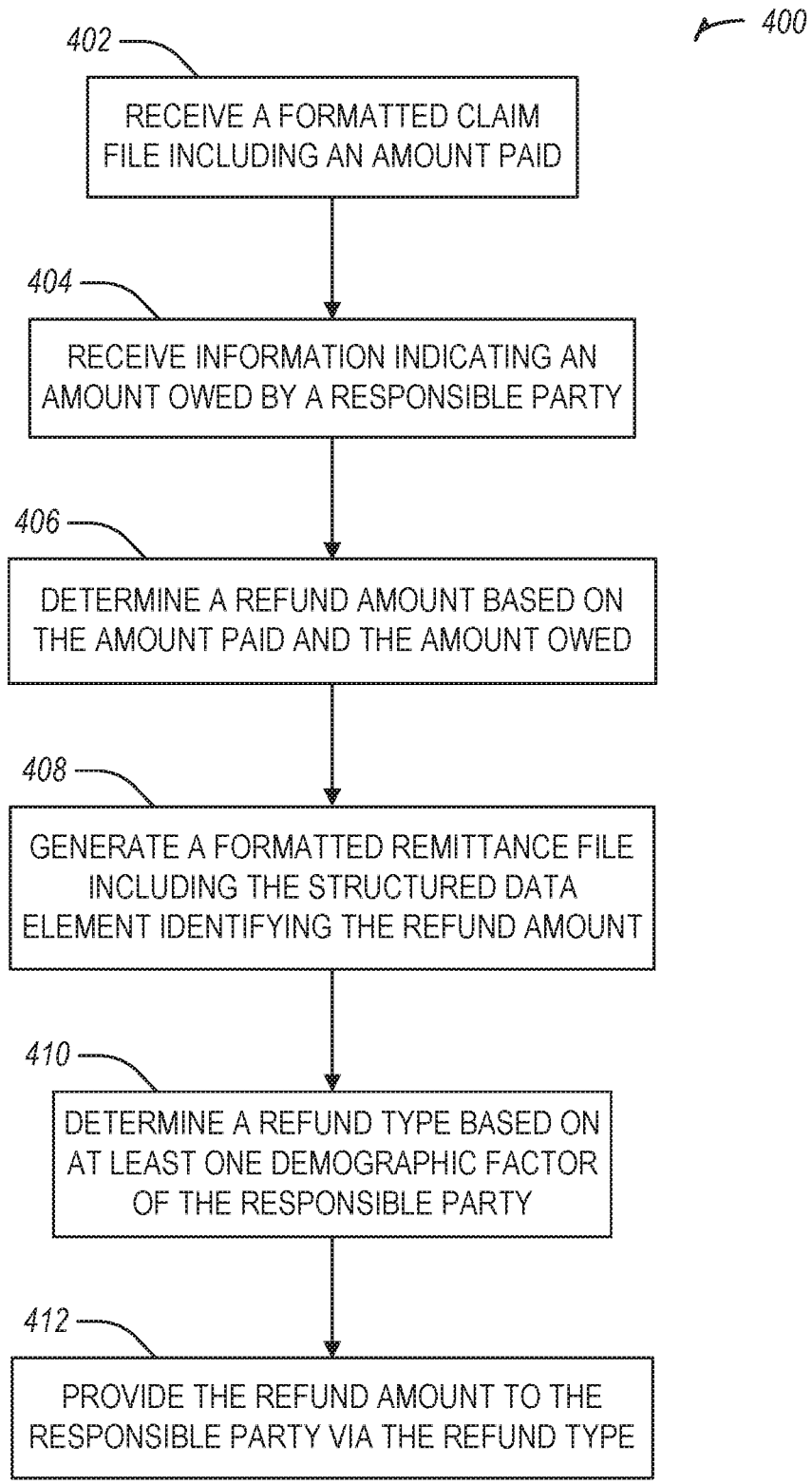
FIG. 4 illustrates a flowchart showing a technique for providing a demographic-based type-specific patient refund in accordance with some embodiments.

FIG. 4 illustrates a flowchart showing a technique 400 for providing a demographic-based type-specific patient refund in accordance with some embodiments. The technique 400 includes an operation 402 to receive a formatted claim file including an amount paid (e.g., from a provider device like 302 of FIG. 3), for example at a processor (e.g., the processor 310 of evaluator 308 of FIG. 3). In an example, the formatted claim file is an EDI 837 formatted file. The technique 400 includes an operation 404 to receive information indicating an amount owed by a responsible party (e.g., from the payer device 316 of FIG. 3 over a network connection). The technique 400 includes an operation 406 to determine a refund amount based on the amount paid and the amount owed. The technique 400 includes an operation 408 to generate a formatted remittance file including the structured data element identifying the refund amount. In an example, the formatted remittance file is an EDI 835 formatted file.

The technique 400 includes an operation 410 to determine a refund type based on at least one demographic factor of the responsible party. The refund type may be determined based on demographics (e.g., age, location, credit score, education level, career, financial sophistication, number of accounts, type of accounts, a predetermined preferred payment type, or the like). The refund type may include a check sent by mail, an e-check, a wire or balance transfer, a prepaid gift card or balance mailed or emailed, a refund to an original payment type (e.g., a credit card, a debit card, a prepaid card, a gift card, etc.), a transfer to an app, a direct deposit to an account, a credit for future services, or the like. For example, the refund type may be a check when the age of the responsible party exceeds a threshold (e.g., above 70 years of age). In another example, the refund type may be a prepaid debit card when the age of the responsible party falls below a threshold (e.g., below 35 years of age). In another example, the threshold ages may be the same (e.g., 50 years of age).

The technique 400 includes an operation 412 to provide the refund amount to the responsible party via the refund type (e.g., sending to a responsible party device, such as device 304 of FIG. 3). The technique may include an operation to determine a responsible party to send the refund. The responsible party may be the patient, a guardian (e.g., when the patient is a minor or incapacitated), an original payer, or the like. The technique may include an optional operation to update the formatted remittance file to adjust the amount owed by the patient to equal the amount paid minus the refund or an indication to notify the provider or the patient that the refund has been issued. The optional operation may include sending the updated formatted remittance file to the healthcare provider or the patient.

Figure 5:
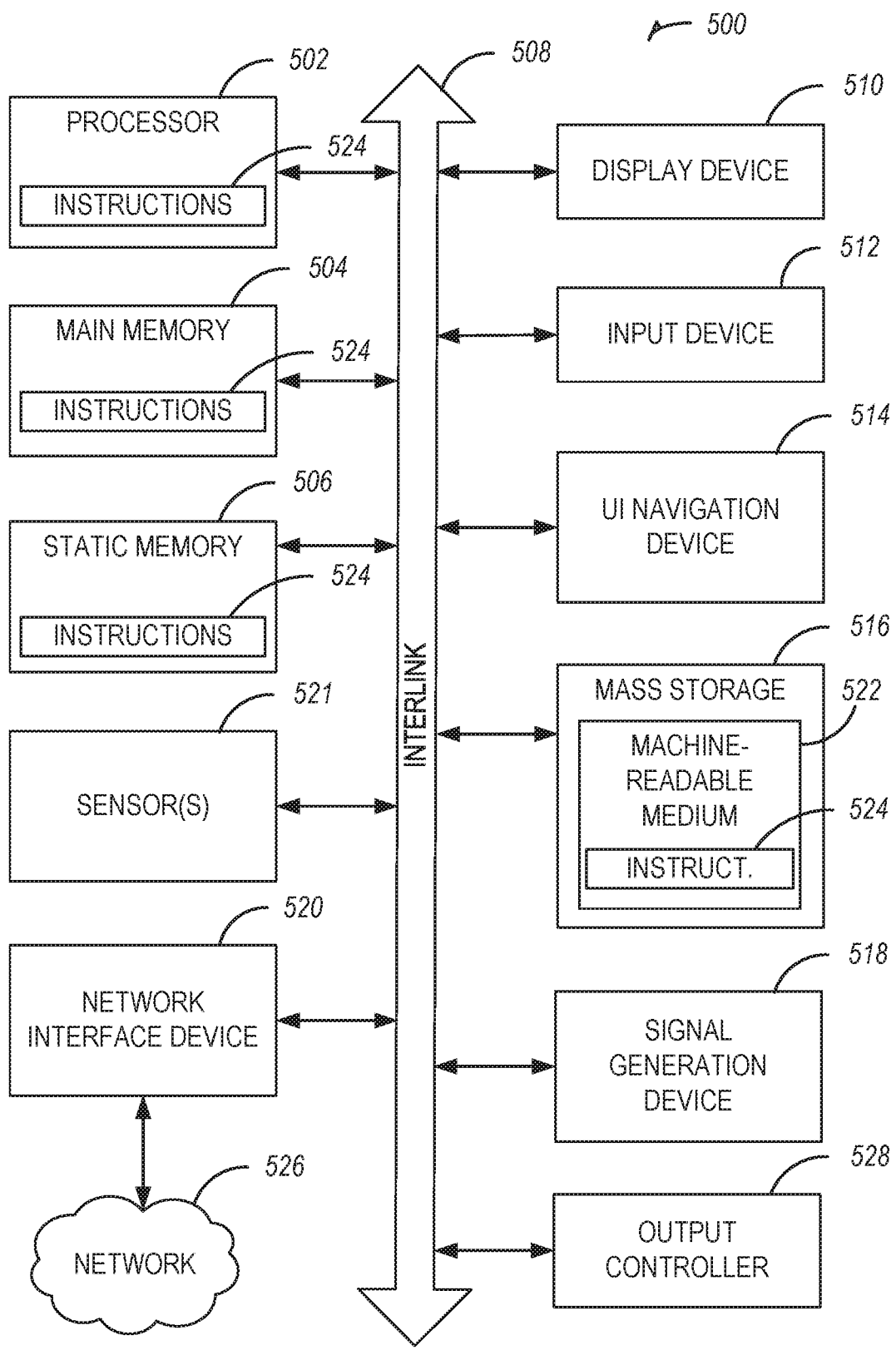
FIG. 5 illustrates generally an example of a block diagram of a machine upon which any one or more of the techniques discussed herein may perform in accordance with some embodiments.

FIG. 5 illustrates generally an example of a block diagram of a machine 500 upon which any one or more of the techniques (e.g., methodologies) discussed herein may perform in accordance with some embodiments. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, alphanumeric input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 that is non-transitory on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In another example, print and mail services may be used for communication. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (IIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for providing a demographic-based type-specific patient refund, the system comprising:
   one or more processors coupled to a memory device, the memory device comprising instructions that, when executed by the one or more processors, cause the one or more processors to:
   receive, from a service of a healthcare provider, a first standardized electronic data interchange (EDI) formatted file including a segment indicating a payment responsibility and an amount paid;
   receive, from a service of a healthcare payer, information indicating an amount owed by a responsible party;
   determine a refund amount based on the amount paid and the amount owed;
   generate a second standardized EDI formatted file including a structured data element identifying the refund amount;
   determine a refund type based on at least one demographic factor of the responsible party, wherein the at least one demographic factor is one of age, location, credit score, education level, career, financial sophistication, number of accounts, type of accounts, or a predetermined preferred payment type; and
   provide, using information from the structured data element, the refund amount to the responsible party via the refund type.

2. The system of claim 1, wherein the first standardized EDI formatted file is a standardized EDI 837 formatted file and wherein the second standardized EDI formatted file is a standardized EDI 835 formatted file.

3. The system of claim 1, wherein the instructions further cause the system to determine a responsible party to send the refund, wherein the responsible party is one of a patient or a guardian of the patient.

4. The system of claim 1, wherein the refund type is one of a check, a prepaid debit card, a remit to a credit card used to transfer the amount paid, or a transfer to an electronic wallet.

5. The system of claim 4, wherein the refund type is the check when the age of the responsible party exceeds a threshold, and the prepaid debit card when the age of the responsible party falls below the threshold.

6. The system of claim 1, wherein the instructions further cause the system to:
update the second standardized EDI formatted file to adjust the amount owed by the patient to equal the amount paid minus the refund; and
send the updated second standardized ED formatted file to the healthcare provider.

7. A method for providing a demographic-based type-specific patient refund, the method comprising:
receiving, at a processor, a first standardized electronic data interchange (EDI) formatted file including a segment indicating a payment responsibility and an amount paid from a computing device of a healthcare provider over a network connection;
receiving, at the processor, information indicating an amount owed by a responsible party from a computing device of a healthcare payer over a network connection;
determining, using the processor, a refund amount based on the amount paid and the amount owed;
generating, using the processor, a second standardized EDI formatted file including a structured data element identifying the refund amount;
determining, using the processor a refund type based on at least one demographic factor of the responsible party, wherein the at least one demographic factor is one of age, location, credit score, education level, career, financial sophistication, number of accounts, type of accounts, or a predetermined preferred payment type; and
providing, using information from the structured data element, the refund amount to the responsible party automatically via the refund type.

8. The method of claim 7, wherein the first standardized EDI formatted file is a standardized EDI 837 formatted file.

9. The method of claim 7, wherein the second standardized EDI formatted file is a standardized EDI 835 formatted file.

10. The method of claim 7, further comprising determining a responsible party to send the refund.

11. The method of claim 10, wherein the responsible party is the patient.

12. The method of claim 10, wherein the patient is a minor and the responsible party is a guardian of the minor.

13. The method of claim 7, wherein the refund type is one of a check, a prepaid debit card, a remit to a credit card used to transfer the amount paid, or a transfer to an electronic wallet.

14. The method of claim 13, w wherein the refund type is the check when the age of the responsible party exceeds a threshold, and the prepaid debit card when the age of the responsible party falls below the threshold.

15. The method of claim 7, further comprising:
updating, using the processor, the second standardized EDI formatted file to adjust the amount owed by the patient to equal the amount paid minus the refund; and
sending the updated second standardized EDI formatted file to the healthcare provider.

16. A non-transitory machine-readable medium including instructions for providing a demographic-based type-specific patient refund, which when performed by a processor of a machine, cause the processor to:
receive, from a service of a healthcare provider, a first standardized electronic data interchange (EDI) formatted file including a segment indicating a payment responsibility and an amount paid;
receive, from a service of a healthcare payer, information indicating an amount owed by a responsible party;
determine a refund amount based on the amount paid and the amount owed;
generate a second standardized EDI formatted file including a structured data element identifying the refund amount;
determine a refund type based on at least one demographic factor of the responsible party, wherein the at least one demographic factor is one of age, location, credit score, education level, career, financial sophistication, number of accounts, type of accounts, or a predetermined preferred payment type; and
provide, using information from the structured data element, the refund amount to the responsible party via the refund type.

17. The non-transitory machine-readable medium of claim 16, wherein the first standardized EDI formatted file is a standardized EDI 837 formatted file and wherein the second standardized EDI formatted file is a standardized EDI 835 formatted file.

18. The non-transitory machine-readable medium of claim 16, wherein the instructions further cause the machine to determine a responsible party to send the refund, wherein the responsible party is one of the patient or a guardian of the patient.

19. The non-transitory machine-readable medium of claim 16, wherein the refund type is one of a check, a prepaid debit card, a remit to a credit card used to transfer the amount paid, or a transfer to an electronic wallet.

20. The non-transitory machine-readable medium of claim 19, wherein the refund type is the check when the age of the responsible party exceeds a threshold, and the prepaid debit card when the age of the responsible party falls below the threshold.

* * * * *

UNITED STATES PATENT AND TRADEMARK OFFICE
CERTIFICATE OF CORRECTION

| | |
|---|---|
| PATENT NO. | : 11,436,304 B1 |
| APPLICATION NO. | : 15/715736 |
| DATED | : September 6, 2022 |
| INVENTOR(S) | : Birgenheier et al. |

It is certified that error appears in the above-identified patent and that said Letters Patent is hereby corrected as shown below:

In the Claims

In Column 25, Line 10, in Claim 6, delete "ED" and insert --EDI-- therefor

In Column 25, Line 52, in Claim 14, before "wherein", delete "w"

Signed and Sealed this
First Day of November, 2022

Katherine Kelly Vidal
*Director of the United States Patent and Trademark Office*